United States Patent [19]

Bertus et al.

[11] 3,960,773

[45] June 1, 1976

[54] CATALYST COMPOSITIONS AND THEIR PREPARATION

[75] Inventors: Brent J. Bertus; Floyd Farha, Jr.; Harlin D. Johnston, all of Bartlesville, Okla.

[73] Assignee: Phillips Petroleum Company, Bartlesville, Okla.

[22] Filed: Nov. 7, 1974

[21] Appl. No.: 521,772

Related U.S. Application Data

[60] Continuation-in-part of Ser. No. 327,722, Jan. 29, 1973, abandoned, which is a division of Ser. No. 81,599, Oct. 16, 1970, Pat. No. 3,745,194.

[52] U.S. Cl. ........................... 252/455 R; 252/456; 252/459; 252/464; 252/466 J; 252/472; 252/473; 252/474
[51] Int. Cl.² ..................... B01J 23/82; B01J 23/84
[58] Field of Search ................ 252/455 R, 456, 459, 252/464, 466 J, 472, 473, 474

[56] References Cited
UNITED STATES PATENTS

| | | | |
|---|---|---|---|
| 3,308,183 | 3/1967 | Bajars | 260/680 |
| 3,480,531 | 11/1969 | Mulaskey | 252/466 J |
| 3,670,044 | 6/1972 | Drehman et al. | 252/472 X |
| 3,691,102 | 9/1972 | Swift | 252/472 X |

*Primary Examiner*—W. J. Shine

[57] ABSTRACT

Organic compounds are dehydrogenated to compounds having a higher degree of unsaturation by contacting the feedstock in the vapor phase in the presence of an oxygen-containing gas with a catalyst containing tin in an oxidized state in combination with at least one of the metals bismuth, cobalt, or nickel in an oxidized state. Representative of such conversions is the oxidative dehydrogenation of butane to 1,3-butadiene over a nickel stannate-containing catalyst. The conversion products are valuable compounds particularly useful as intermediates for the preparation of polymeric materials such as synthetic rubbers and the like.

17 Claims, No Drawings

CATALYST COMPOSITIONS AND THEIR PREPARATION

This application is a continuation-in-part of application Ser. No. 327,722, filed Jan. 29, 1973, now abandoned, which was a division of application Ser. No. 81,599, filed Oct. 16, 1970, now U.S. Pat. No. 3,745,194.

The present invention relates to chemical compositions. More particularly, the invention relates to catalyst compositions, their preparation and to catalytic processes employing such compositions, e.g., processes for effecting the dehydrogenation of hydrocarbons.

As a general rule, the unsaturated hydrocarbons have a greater economic value than saturated or paraffinic hydrocarbons. For example, butenes are more valuable than butanes and butadiene is more valuable than either. Presently, diolefins such as 1,3-butadiene and isoprene are in high demand, particularly for conversion to polymeric materials for use in the rubber industry. The unsaturated hydrocarbons are generally produced by hydrocarbon conversion methods, with the dehydrogenation of more saturated feedstocks being a widely used method of synthesizing such materials. While noncatalytic thermal dehydrogenation processes are known, such processes are generally not economically desirable for preparing olefins and diolefins because of low conversion and yields to desired products, extensive undesirable side reactions which take place in such processes, and the large capital requirements for equipment capable of handling temperature requirements and the large volumes of materials which must necessarily be handled.

As a consequence, a large number of catalytic processes have been developed for the dehydrogenation of organic feedstocks to more unsaturated materials. Thus, there are known catalytic processes for the dehydrogenation of paraffinic feedstocks in the absence of oxygen, in the presence of oxygen, and in the presence of hydrogen. Processes are also known for the dehydrogenation of olefins such as butenes to diolefinic materials such as the butadienes in the absence of oxygen, in the presence of oxygen and in the presence of hydrogen. At least certain of these processes have been found quite effective in converting paraffinic hydrocarbons to monoolefinic unsaturated materials and mono-unsaturated hydrocarbons such as monoolefins to the diolefinic material. The direct conversion of saturated hydrocarbons to substantial amounts of diolefins, though highly desirable, is very elusive because such direct conversions generally result in low per pass conversions or low selectivities or both.

It has now been discovered that saturated paraffins such as butane can be directly converted in one step to diolefinic materials with sufficient per pass conversions and selectivities which, when combined with other advantages, provide a process which can be economically attractive. One of these advantages is the nature of the by-products formed. A substantial portion of the products other than the valuable monoolefins or diolefins consists of other olefinic materials which are more valuable than the starting feed and which can be considered valuable salable products. These additional by-products appear to be obtained by a cracking operation because they have fewer carbon atoms per molecule than the starting feed hydrocarbon. Specifically, the cracking side reaction produces a substantial amount of lower molecular olefinic products with only small amounts of carbon monoxide and carbon dioxide or other typical cracking products such as coke and heavy aromatic compounds which are of relatively little value and which frequently cause difficulties in separation operations.

The present invention provides a novel catalyst and a novel process for the conversion of hydrocarbon feedstocks to hydrocarbons having a greater degree of unsaturation and which have the same or lower number of carbon atoms as in the hydrocarbon feed. According to this invention, hydrocarbon feedstock can be converted directly to hydrocarbons having a greater degree of unsaturation by contacting said feedstock under dehydrogenation conditions in the vapor phase in the presence of molecular oxygen with a catalytic material comprising tin in an oxidized state in association with at least one of the metals bismuth, cobalt or nickel in an oxidized state. Thus, paraffinic hydrocarbons can be converted in good yields diolefins and/or monoolefins and monoolefins can be converted to diolefins. The invention is particularly applicable for the production of diolefins from paraffins and particularly useful results are obtained by the dehydrogenation of butane to 1,3-butadiene.

The hydrocarbon feedstocks which are applicable for the oxidative dehydrogenation processes of the present invention comprise dehydrogenatable aliphatic hydrocarbons having from about 4 to about 10 carbon atoms per molecule and at least one

grouping. These can be branched or unbranched and include paraffins as well as monoolefins, but paraffins are presently preferred. The conversion of butane has been found particularly advantageous by the process of the invention. Some specific examples of other feeds include isobutane, pentane, methylbutanes, hexane, 2-methylhexane, octane, 2,4-dimethyloctane, butene-2, 2-methylbutene-1, hexene-2, octene-1, 3-methylnonene-4, and the like, and mixtures of such compounds.

The novel catalysts of the present invention comprise tin associated with at least one of bismuth, cobalt or nickel. These elements are not in the elemental state but are combined with sufficient oxygen to form one or more neutral compounds, for example, bismuth stannate. The atomic proportions of tin to the bismuth, cobalt or nickel are in the range of from about 3:1 to about 1:3, preferably from about 2:1 to about 1:2, in the catalyst. Optionally, but preferably, the above catalyst is further associated with a catalytic support material. The presently preferred support material is a catalytic grade silica, alumina, or silica-alumina. The support material, when used, will comprise about 10 to about 90, preferably from about 30 to about 60, weight percent of the total catalyst composition.

The above-described catalytic composition can still further, optionally, be associated with a catalyst-modifying quantity of a Group IA or a Group IIA metal. When present, the alkali or alkaline earth metal will be present in the catalytic composition in the range of from about 0.1 to about 10 weight percent, based upon the weight of the above-described catalyst composition.

Still further, the catalyst can comprise, if desired, a modifying amount of antimony and/or arsenic. These materials will generally be present in the catalyst, when utilized, in amounts ranging from about 0.1 to about 10 weight percent, based upon the weight of the above-described catalyst composition.

Thus, in one embodiment, there is provided a catalyst composition consisting of tin, nickel and arsenic or antimony and, optionally, a Group IA or Group IIA metal in the amounts and proportions described above. These elements are combined with sufficient oxygen to form one or more neutral compounds. Optionally, the above catalyst can be associated with a catalyst support material as described above.

The catalysts of the present invention can be prepared by any suitable method. Conventional methods such as coprecipitation, impregnation, or dry-mixing can be used. In general, any method can be used which will provide a composition containing the above-described elements in the above-described proportions and which will have a catalytic surface area of at least 1 square meter/gram.

Thus, a tin compound and at least one compound of bismuth, cobalt, or nickel are combined in any suitable way. Substantially any tin compound or any bismuth, cobalt or nickel compound can be employed in the catalyst composition so long as none of the compounds are deleterious to the final dehydrogenation catalyst and essentially all of the elements in the compounds used, other than the tin, bismuth, cobalt or nickel, are removed from the final catalyst by prior washing or by volitilization.

Suitable tin compounds include any such compound which is soluble or dispersible in water and can include both stannous or stannic compounds. Examples of such compounds includes potassium stannate, stannic fluoride, stannous chloride, stannic bromide, stannous iodide, stannic sulfate, stannic acetate, stannic oxide, stannic tartrate, stannic nitrate, and the like and mixtures thereof.

Similarly, suitable bismuth, cobalt or nickel compounds can be used. These can include both organic or inorganic compounds. Some examples of these are nickel oxide, nickel acetylacetonate, bismuth bromide, cobalt nitrate, nickel nitrate, nickel acetate, bismuth oxychloride, cobalt chloride, nickel chloride, and the like and mixtures thereof.

Similarly, examples of catalyst-modifying materials comprising one or more alkali or alkaline earth metal compounds or arsenic or antimony compounds can include lithium nitrate, sodium carbonate, potassium chloride, rubidium acetate, cesium nitrate, magnesium bromide, calcium chloride, strontium tartrate, sodium arsenate, arsenic acid, antimony trioxide, antimony pentoxide, antimony chloride, triphenylarsine, and the like and mixtures thereof.

A convenient preparation is to coprecipitate suitable catalyst-forming compounds from aqueous solutions followed by conventional aging, washing, drying, calcining, pelletizing and the like. When a catalyst support is used, it can conveniently be introduced during the coprecipitation stage of catalyst preparation. Alternatively, a solid catalyst support, generally in the finished form of a pellet, sphere, or particle, can be impregnated with solutions of a tin compound and of a suitable bismuth, cobalt, or nickel compound. The impregnated solid can then be dried and calcined. When other catalyst-modifying agents are used, they can be introduced into the catalyst either before, during, or after the tin and the bismuth, cobalt or nickel compounds have been associated with the support.

Whichever catalyst preparation technique is used, the catalyst is activated prior to contact with the feed hydrocarbons by a calcination step. Thus, the finished catalyst is calcined in an oxygen-containing gas such as air at a temperature in the range of from about 900° to about 1500°F for a time in the range of about 1 to about 24 hours, or until the catalyst is active for carrying out the oxidative dehydrogenation step.

The hydrocarbon feedstocks can be dehydrogenated according to the process and with the catalyst of the present invention at temperatures in the range of from about 800° to about 1200°F, preferably from about 950° to about 1100°F at any convenient pressure such as from about 7 to about 250 psia, and at a hydrocarbon:oxygen mol ratio of from about 1:0.5 to about 1:4. The presence of steam is frequently beneficial and a steam:hydrocarbon mol ratio up to about 20:1 can be used. The hydrocarbon feed rate will generally be in the range of from about 50 to about 800 GHSV. The fixed catalyst bed is the preferred mode of contact but other modes, such as the fluidized bed, can also be used.

The dehydrogenation process of this invention is ordinarily carried out by forming a mixture, preferably preheated, of the hydrocarbon feed, the oxygen-containing gas, and the steam (when used) and passing this mixture over the catalyst at the selected temperature. The effluent from the reaction zone is subjected to any suitable separation method to isolate and recover the desired products. Unconverted feeds or partially converted materials can be recycled.

The invention can be illustrated by the following examples.

EXAMPLE I

Preparation of Catalysts

Several tin-containing oxidative dehydrogenation catalysts were prepared in which the tin was associated with each of bismuth, nickel and cobalt. Each catalyst also contained 40 weight percent alumina (Alon-C, a finely divided, nonporous, flame-hydrolyzed alumina commercially available from Cabot Corporation).

The catalysts were prepared by mixing bismuth stannate, nickel stannate, or cobalt stannate with the alumina with just enough distilled water to make a slurry. Both the alumina and the metal stannates were in the powdered state. The slurry was dried at 300°F and calcined at 1200°F in air for about 16 hours. The resulting caked solid was then granulated to 8–20 mesh.

For purposes of comparison, a similar iron-containing catalyst was prepared from ferrous stannate.

EXAMPLE II

Oxidative Dehydrogenation of Butane

The above-described catalysts were charged into a fixed bed reactor and used in several runs in which butane was dehydrogenated in the presence of air and steam (in certain of the runs). The essential conditions and the results of these runs are shown in the following table.

Table I

| Run | Temp. °F | Feed rates (GHSV) C₄H₁₀ | Air | Steam | Con. | Mols/100 Mols of Feed Mod.* | C₄H₈+C₄H₆ | C₂H₄+C₃H₆ |
| --- | --- | --- | --- | --- | --- | --- | --- | --- |
| 1 60% bismuth stannate 40% alumina | 1050 | 18 | 550 | 0 | 34.3 | 89 | 19.2 | 14.0 |
| 2 60% bismuth stannate 40% alumina | 1000 | 300 | 1500 | 0 | 23.0 | 89 | 16.0 | 4.0 |
| 3 60% bismuth stannate 40% alumina | 1000 | 100 | 300 | 0 | 34.0 | 91 | 22.0 | 9.0 |
| 4 60% cobalt stannate 40% alumina | 1050 | 50 | 250 | 600 | 36.0 | 59.5 | 15.4 | 6.0 |
| 5 60% nickel stannate 40% alumina | 1000 | 50 | 250 | 250 | 27.0 | 74 | 18.0 | 5.7 |
| 6 60% ferrous stannate 40% alumina | 1050 | 100 | 500 | 0 | 25.9 | 46.7 | 8.7 | 3.4 |

*Modivity = A simplified selectivity based on gas phase products only. Here, it represents conversion to $C_4H_8$, $C_4H_6$ and $C_2H_4$, $C_3H_6$. (Conversions are based on a $C_4$ feed basis).

The data in the table show that the catalysts containing tin and bismuth, tin and nickel, and tin and cobalt show substantial activity for the conversion of butane to desirable dehydrogenated products such as butenes and butadienes, as well as to desirable cracked products such as ethylene and propylene. Butadiene was a significant amount of the $C_4$ products. For comparison, the comparable tin and iron-containing catalyst shows less conversion and/or selectivity in this reaction.

EXAMPLE III

A Ni/Sn/O catalyst was prepared by preparing separate solutions of nickel nitrate, potassium stannate and potassium hydroxide in amounts sufficient to provide a Ni:Sn atomic ratio of about 3:1 in the finished catalyst. The three solutions were then added, simultaneously and dropwise, into a stirred container of water while maintaining a pH of about 8–9. The resulting wet gel was filtered and washed with distilled water. Portions of the wet gel were impregnated with arsenic acid to give the amounts of arsenic as shown below. The catalyst compositions were dried, calcined for 3 hours at 1100°F, then ground and screened to a 20–40 mesh size.

The catalysts were used in the oxidative dehydrogenation of n-butane in separate runs. The runs were carried out in a fixed bed reactor at 1100°F and at atmospheric pressure. The feed rate for the butane was 500 GHSV. The oxygen:butane mol ratio was about 1.1:1 and the steam:butane mol ratio was about 10:1. The results of these runs are shown in Table II:

Table II

| Wt.% As | Catalyst Age, hr. | Conversion, % | Modivity, % |
| --- | --- | --- | --- |
| None | 18.5 | 30.1 | 4.6 |
| 2 | 12 | 23.7 | 40.2 |
| 4 | 12 | 25.6 | 64.5 |
| 6 | 12 | 24.8 | 64.4 |
| 8 | 12 | 24.2 | 71.9 |

The above data show that the catalysts containing arsenic show substantially improved activity for the dehydrogenation of butane when compared with the unmodified Ni/Sn/O catalyst.

While certain embodiments of the invention have been described for illustrative purposes, the invention is not limited thereto. Various other modifications or embodiments of the invention will be apparent to those skilled in the art in view of this disclosure. Such modifications or embodiments are within the spirit and scope of the disclosure.

We claim:

1. A catalyst composition consisting of tin, nickel, at least one metal selected from the group consisting of arsenic and antimony and, optionally, at least one metal selected from the group consisting of Group Ia and Group IIa metals, said elements in combination with sufficient oxygen to form one or more neutral compounds, said composition formed by dry mixing a tin compound and a nickel compound in amounts sufficient to provide an atomic ratio of tin to nickel in the finished catalyst in the range of 1:3 to 3:1, said tin and nickel compounds being selected from the group consisting of their respective oxides and salts, a quantity of an antimony compound, an arsenic compound or a combination thereof sufficient to provide from about 0.1 to about 10 weight percent of said antimony or said arsenic based upon the combined weight of said tin and nickel and oxygen combined therewith, said arsenic compound selected from the group consisting of the oxides, salts and acids thereof, said antimony compound selected from the group consisting of the oxides and salts thereof, and, optionally, a quantity of a Group Ia metal salt, a Group IIa metal salt or combination thereof sufficient to provide from about 0.1 to about 10 weight percent of said Group Ia metal or said Group IIa metal based upon the combined weight of said tin and nickel and oxygen combined therewith, and thereafter calcining said composition.

2. The composition of claim 1 wherein said tin:nickel atomic ratio is in the range of 1:2 to 2:1.

3. The composition of claim 1 further including at least one support material selected from the group consisting of silica, alumina and silica-alumina, wherein the amount of said support is about 10 to about 90 weight percent based upon the weight of the total composition.

4. A catalyst composition consisting of tin, nickel, at least one metal selected from the group consisting of arsenic and antimony and, optionally, at least one metal selected from the group consisting of Group Ia and Group IIa metals, said elements in combination with sufficient oxygen to form one or more neutral compounds, said composition formed by coprecipitating said tin and said nickel from aqueous solution of tin and nickel compounds, wherein the amount of each compound is sufficient to provide an atomic ratio of tin to nickel in the finished catalyst in the range of 1:3 to 3:1, said tin and nickel compounds being selected from the group consisting of their respective oxides and salts; thereafter impregnating the resulting coprecipitate with a solution of an antimony compound, an arsenic compound or combination thereof sufficient to provide from about 0.1 to about 10 weight percent of said antimony or said arsenic based upon the combined weight of said tin and nickel and oxygen combined therewith, said arsenic compound selected from the group consisting of the oxides, salts and acids thereof, said antimony compound selected from the group consisting of the oxides and salts thereof, and, optionally, impregnating said coprecipitate with a solution of a Group Ia metal salt, a Group IIa metal salt or combination thereof sufficient to provide from about 0.1 to about 10 weight percent of said Group Ia metal or said Group IIa metal based upon the combined weight of said tin and nickel and oxygen combined therewith; drying the resulting composition; and thereafter calcining said composition.

5. The composition of claim 4 further including at least one support material selected from the group consisting of silica, alumina and silica-alumina, wherein the amount of said support is about 10 to about 90 weight percent based upon the weight of the total composition.

6. The composition of claim 5 wherein said support is introduced during the coprecipitation of said tin and said nickel.

7. The composition of claim 5 wherein said support is introduced subsequent to said drying step.

8. The catalyst composition of claim 4 wherein said Sn/Ni atomic ratio is about 1:3 and the amount of said arsenic is about 2 weight percent.

9. The catalyst composition of claim 4 wherein said Sn/Ni atomic ratio is about 1:3 and the amount of said arsenic is about 4 weight percent.

10. The catalyst composition of claim 4 wherein said Sn/Ni atomic ratio is about 1:3 and the amount of said arsenic is about 6 weight percent.

11. The catalyst composition of claim 4 wherein said Sn/Ni atomic ratio is about 1:3 and the amount of said arsenic is about 8 weight percent.

12. The composition of claim 4 wherein said tin:-nickel atomic ratio is in the range of 1:2 to 2:1.

13. A catalyst composition consisting of tin, nickel, at least one metal selected from the group consisting of arsenic and antimony, and optionally, at least one metal selected from the group consisting of Group Ia and Group IIa metals, said elements in combination with sufficient oxygen to form one or more neutral compounds, and at least one support material selected from the group consisting of silica, alumina and silica-alumina, wherein the amount of said support is about 10 to about 90 weight percent based on the weight of the total composition, said composition formed by impregnating said support with a solution of a tin compound selected from the group consisting of the oxides and salts of tin, and a solution of a nickel compound selected from the group consisting of the oxides and salts of nickel in amounts of each of said tin compound and said nickel compound to provide an atomic ratio of tin to nickel in the finished catalyst in the range of 1:3 to 3:1, thereafter impregnating said support with a solution of an antimony compound, an arsenic compound or combination thereof sufficient to provide from about 0.1 to about 10 weight percent of said antimony or said arsenic based upon the combined weight of said tin and nickel and oxygen combined therewith, said arsenic compound selected from the group consisting of the oxides, salts and acids thereof, said antimony compound selected from the group consisting of the oxides and salts thereof; and optionally, impregnating said support with a solution of a Group Ia metal salt, a Group IIa metal salt or combination thereof sufficient to provide from about 0.1 to about 10 weight percent of said Group Ia metal or said Group IIa metal based upon the combined weight of said tin and nickel and oxygen combined therewith; drying the resulting composition; and thereafter calcining said composition.

14. A catalyst composition consisting of tin, nickel, at least one metal selected from the group consisting of arsenic and antimony, and at least one metal selected from the group consisting of Group Ia metals and Group IIa metals, said elements in combination with sufficient oxygen to form one or more neutral compounds, said composition formed by coprecipitating said tin and said nickel and at least a portion of said Group Ia metal, said Group IIa metal or combination thereof from aqueous solution of tin and nickel compounds and Group Ia salts, Group IIa salts or combination thereof, wherein the amount of each of said tin and nickel compounds is sufficient to provide an atomic ratio of tin to nickel in the finished catalyst in the range of 1:3 to 3:1 and wherein the amount of said Group Ia metal salt, said Group IIa metal salt or combination thereof is sufficient to provide from about 0.1 to about 10 weight percent of said Group Ia metal, said Group IIa metal or combination thereof based upon the combined weight of said tin and nickel and oxygen combined therewith, said nickel and tin compounds being selected from the group consisting of their respective oxides and salts; thereafter impregnating the resulting coprecipitate with a solution of an antimony compound, an arsenic compound or combination thereof sufficient to provide from about 0.1 to about 10 weight percent of said antimony or said arsenic based upon the combined weight of said tin and nickel and oxygen combined therewith, said arsenic compound selected from the group consisting of the oxides, salts and acids thereof, said antimony compound selected from the group consisting of the oxides and salts thereof; and, optionally, impregnating said coprecipitate with a solution of a Group Ia metal salt, a Group IIa metal salt or combination thereof sufficient to provide the remainder of the desired quantity of said Group Ia or Group IIa metal; drying the resulting composition; and thereafter calcining said composition.

15. The catalyst composition of claim 14 further including at least one support material selected from the group consisting of silica, alumina and silica-alumina, wherein the amount of said support is about 10 to about 90 weight percent based upon the weight of the total composition.

16. The composition of claim 15 wherein said support is introduced during the coprecipitation of said tin and said nickel.

17. The composition of claim 15 wherein said support is introduced subsequent to said drying step.

* * * * *